United States Patent [19]

Baule et al.

[11] Patent Number: 4,918,209

[45] Date of Patent: Apr. 17, 1990

[54] PRODUCTION OF OXIMINOSILANES

[75] Inventors: Pierre Baule, Saint-Symphorien d'Ozon; Francois Chizat, Bron, both of France

[73] Assignee: Rhone-Poulenc Chimie, Courbevoie, France

[21] Appl. No.: 164,897

[22] Filed: Mar. 7, 1988

[30] Foreign Application Priority Data

Mar. 5, 1987 [FR] France ................................ 87 03206

[51] Int. Cl.$^4$ .............................................. C07F 7/10
[52] U.S. Cl. .................................................. 556/422
[58] Field of Search ........................................ 556/422

[56] References Cited

U.S. PATENT DOCUMENTS 3,697,568 10/1972 Boissieras et al. .................. 556/422
4,033,991 7/1977 Shinohara ...................... 556/422 X
4,380,660 4/1983 Mathew et al. ...................... 556/422
4,384,131 5/1983 Kanner et al. ...................... 556/422
4,400,527 8/1983 Mathew et al. ...................... 556/422
4,766,231 8/1988 Zoche ................................. 556/422

Primary Examiner—Paul F. Shaver
Attorney, Agent, or Firm—Burns, Doane, Swecker & Mathis

[57] ABSTRACT

The oximinosilanes, e.g., methyltris(methyl ethyl ketoximo)silane and vinyltris(methyl ethyl ketoximo)silane, are improvedly produced by continuously charging a halogenated silane, an oxime, ammonia gas and an organic solvent medium into a stirred reaction zone, removing precipitated ammonium halide from the medium of reaction), and recovering product oximinosilane from the organic solvent phase, e.g., by distillation.

15 Claims, 1 Drawing Sheet

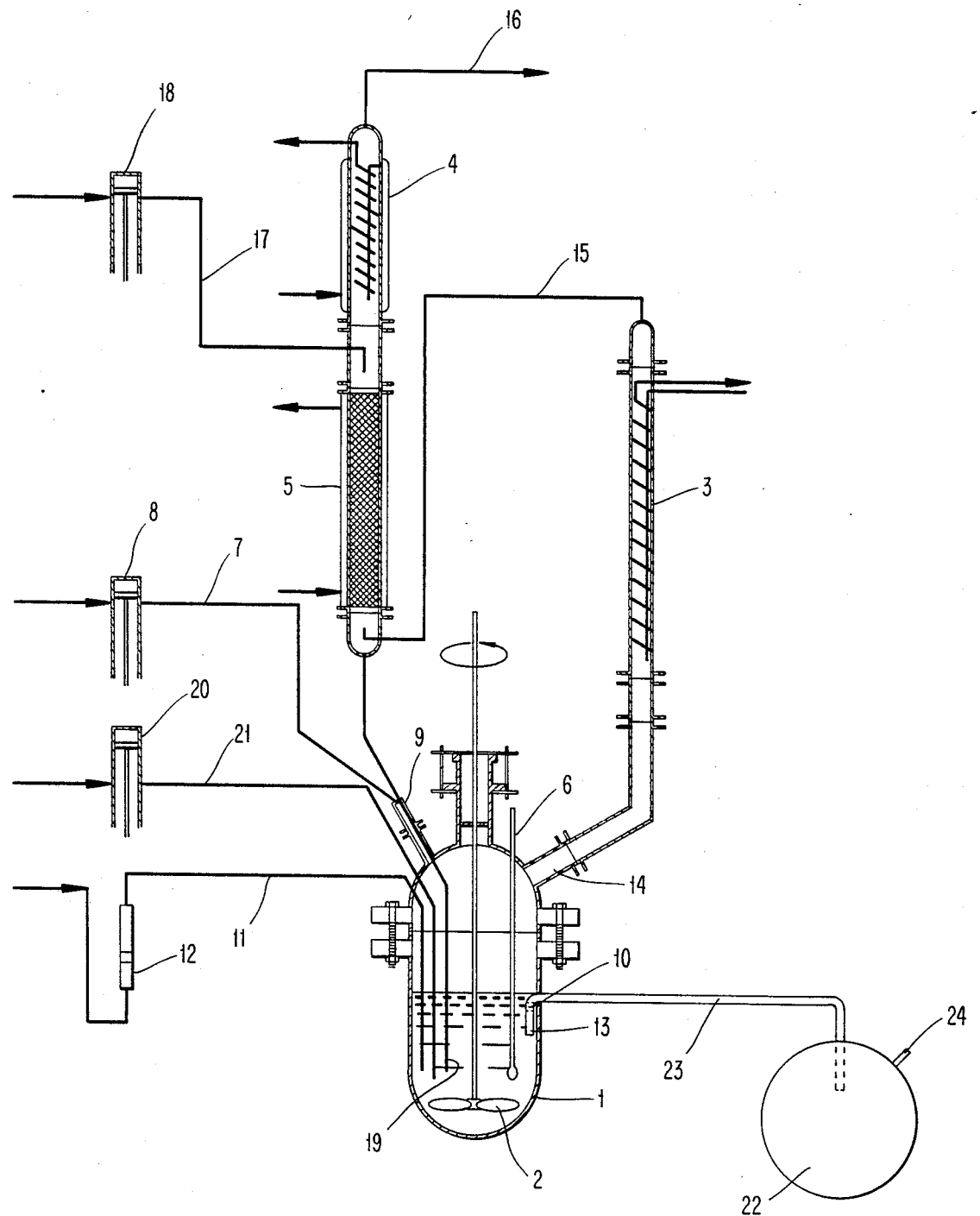

PRODUCTION OF OXIMINOSILANES

BACKGROUND OF THE INVENTION

1. Field of the Invention

The present invention relates to a process for the continuous production of oximinosilanes (also known as the iminooxysilanes) such as, in particular, methyltris(methyl ethyl ketoximo)silane or vinyltris(methyl ethyl ketoximo)silane, by reacting methyltrichlorosilane or vinyltrichlorosilane with methyl ethyl ketoxime.

2. Description of the Prior Art

The preparation of oximinosilanes is known to this art. Compare, for example, European Patent Application No. 82,324, published June 29, 1983, which describes a process in which an oxime and a halogenated silane are reacted with each other, the oxime being in a molar ratio at least equal to 2n:1 relative to the halogenated silane, representing the number of halogen atoms in the said halogenated silane. The excess oxime thus acts as an acceptor for the HCl formed in the reaction. In this '324 European Application, it is mentioned (page 10, lines 5-11) that the process may be carried out continuously and that the residence time of the reagents is then on the order of 1 to 3 hours, although in Examples 1 to 12, no process is described in which the reagents are injected simultaneously and continuously into the reactor. Moreover, the process described in this European Application No. 82,324 requires phase separations, separations and alkalizations to be carried out in apparatus equipped with stirrers.

Other methods for the preparation of oximinosilanes are described in this European Application No. 82,324, pages 1 and 2. However, in these processes of the prior art, organic bases such as triethylamine are, for example, employed as an acceptor for hydrochloric acid. It is also described that these compounds may lead to risks of explosion during the distillation. In other processes, the sodium salt of the oxime is reacted with a stoichiometric quantity of chlorosilane. Such procedure, notably, presents the disadvantages associated with requiring an additional stage for the preparation of the sodium salt of the oxime, and the separation of the sodium chloride formed during the reaction is cumbersome.

SUMMARY OF THE INVENTION

Accordingly, a major object of the present invention is the provision of an improved process for preparing oximinosilanes which is conspicuously devoid of those disadvantages and drawbacks to date characterizing the state of this art.

Another object of the present invention is the provision of an improved process for preparing oximinosilanes in which the reagents and a reaction solvent are introduced continuously and simultaneously into the reactor/reaction zone.

Another object of the present invention is a process in which the acceptor for the hydrochloric acid formed is a gaseous material.

Yet another object of the present invention is a continuous process having increased safety.

Yet another object of the present invention is a process in which the solvent employed is non-inflammable.

Another object of the present invention is a process in which the solvent employed is an organic compound having a boiling point below 60° C.

Another object of the present invention is a process in which the residence time of the products in the reactor is less than one hour, preferably between 10 and 40 minutes.

Another object of the present invention is a process in which there is no need to cool the reactor.

Another object of the present invention is a process in which the product oximinosilanes are only slightly colored or colorless.

Still another object of the present invention is a continuous process in which the yields are generally equal to or even greater than 80%, especially when the oximinosilanes prepared are methyltris(methyl ethyl ketoximo)silane or vinyltris(methyl ethyl ketoximo)silane.

Briefly, the present invention features a process for the continuous production of oximinosilanes, wherein:

(a) the following reagents are continuously and simultaneously injected into a reactor equipped with a stirrer:
  (i) an organic solvent,
  (ii) ammonia gas,
  (iii) a halogenated silane of the formula $R_{4-n}SiX_n$ in which X represents a halogen and R represents an alkyl radical containing from 1 to 15 carbon atoms, preferably from 1 to 6 carbon atoms, an alkenyl radical containing from 2 to 15 carbon atoms, preferably from 2 to 6 carbon atoms, an aryl, aralkyl or cycloalkyl radical containing from 5 to 15 carbon atoms, and optionally halogenated such radicals which are inert under the condition of the reaction, with n being equal to 1, 2, 3 or 4, and
  (iv) an oxime of the formula $R'R''C=N-OH$, in which R' and R'' represent a hydrogen atom, an alkyl radical containing from 1 to 15 carbon atoms, preferably from 1 to 6 carbon atoms, an alkenyl radical containing from 2 to 15 carbon atoms, preferably from 2 to 6 carbon atoms, an aryl, cycloalkyl, cycloalkenyl, aralkyl or alkylaryl radical containing from 5 to 15 carbon atoms, or optionally halogenated such radicals which are inert under the condition of the reaction, with the proviso that R' and R'' may together form an alkylene group such as $CH_{2-m}$, in which m represents 3 to 7, or halogenated such groups which are inert under the condition of the reaction; with the ratio $$\frac{\text{number of moles of NH}_3}{\text{number of moles of R}_{4-n}\text{SiX}_n \text{ multiplied by } n}$$

ranging from 1.04 to 1.46; and the ratio $$\frac{\text{number of moles of oxime}}{\text{number of moles of R}_{4-n}\text{SiX}_n \text{ multiplied by } n}$$

ranging from 1 to 1.2, (b) collecting continuously the reaction mass which exits the reactor by an overflow means;
(c) removing a precipitate of $XNH_4$ from this reaction mass and distilling the organic liquid phase in order to recover therefrom the oximinosilane.

BRIEF DESCRIPTION OF THE DRAWINGS

The Figure of Drawing is a diagrammatic/schematic illustration of appropriate process/apparatus according to the invention.

DETAILED DESCRIPTION OF THE PREFERRED EMBODIMENTS OF THE INVENTION

More particularly according to the present invention, as mentioned above, the acid acceptor which immobilizes the hydrochloric acid formed during the reaction is ammonia gas.

The solvent employed is an inert organic solvent having a boiling point generally below 60° C., this solvent preferably being non-inflammable. Among the solvents which are suitable for carrying out the subject process, the perchlorofluorinated alkanes have proved very advantageous. Representative are, in particular, trichlorotrifluoroethanes and more especially 1,1,2-trichloro-1,2,2-trifluoroethane, the boiling point of which is 47.7° C. at normal pressure, or mixtures thereof. Such compounds are marketed by ATOCHEM under the trademark FLUGENE.

The halogenated silane employed in the process of the invention has the formula $R_{4-n}SiX_n$, in which X represents a halogen atom, n is equal to 1, 2, 3 or 4 and R is as defined above. As specific examples of silanes which can be employed in the process according to the present invention, representative are tetrachlorosilane, trimethylchlorosilane, dimethyldichlorosilane, methyltrichlorosilane, methylethyldichlorosilane, ethyltrichlorosilane, diethyldichlorosilane, triethylchlorosilane, n-propyltrichlorosilane, isopropyltrichlorosilane, 2-chloroethyltrichlorosilane 3-chloropropyltrichlorosilane, triethylchlorosilane, vinyltrichlorosilane, vinylmethyldichlorosilane, propenyltrichlorosilane, allyltrichlorosilane, phenyltrichlorosilane and benzyltrichlorosilane. Preferably, in the silane having the formula $R_{4-n}SiX_n$, n is equal to 3, X represents a chlorine atom and R represents a methyl, ethyl or vinyl radical.

The oxime employed in the process according to the present invention has the formula $R'R''C=N-OH$, in which R' and R'' are as defined above. R' and R'' which may be identical or different, are preferably methyl, ethyl, propyl, butyl, pentyl, hexyl, vinyl, butenyl, cyclopentyl, cyclohexyl, cyclooctyl, 3-methyl-1-cyclohexyl, cyclopentenyl, cyclohexenyl, phenyl, tolyl, xylyl or benzyl radicals. As specific examples of such oximes, particularly representative are:

| Formula | Name |
|---|---|
| $CH_3-CH=NH-OH$ | acetaldehyde oxime |
| $(CH_3)_2C=N-OH$ | acetone oxime |
| $CH_3+CH_2\overline{)_3}C-CH_3$<br>$\phantom{CH_3+CH_2\overline{)_3}}\|\|$<br>$\phantom{CH_3+CH_2\overline{)_3}C}N-OH$ | 2-hexanone oxime |
| $C_3H_7-CH=N-OH$ | 1-butyraldehyde oxime |
| $CH_2=CH-CH_2-C-CH_3$<br>$\phantom{CH_2=CH-CH_2-}\|\|$<br>$\phantom{CH_2=CH-CH_2-C}N-OH$ | 4-penten-2-one oxime |
| $CH_3-CH_2$<br>$\phantom{CH_3-}\backslash$<br>$\phantom{CH_3-CH_2}C=N-OH$<br>$\phantom{CH_3-}/$<br>$CH_3$ | methyl ethyl ketone oxime (butanone oxime) |
| $C_6H_5-CH=N-OH$ | benzaldehyde oxime |
| $C_6H_5-C=N-OH$<br>$\phantom{C_6H_5-}\|$<br>$\phantom{C_6H_5-}CH_3$ | acetophenone oxime |
| $(C_6H_5)_2-C=N-OH$ | benzophenone oxime |
| $C_6H_5-CH_2$<br>$\phantom{C_6H_5-}\backslash$<br>$\phantom{C_6H_5-CH_2}C=N-OH$<br>$\phantom{C_6H_5-}/$<br>$C_2H_5$ | benzyl ethyl ketone oxime |
| $C_6H_5-CH=CH-CH=N-OH$ | cinnamaldehyde oxime |
| cyclohexyl-$C=N-OH$, $CH_3$ | cyclohexyl methyl ketone oxime |
| cyclopentyl=$N-OH$ | cyclopentanone oxime |
| cyclohexyl=$N-OH$ | cyclohexanone oxime |
| $CH_3$-cyclopentyl=$N-OH$ | 5-methyl-1-cyclopentanone oxime |
| $CH_3$-cyclohexyl=$N-OH$ | 5-methyl-1-cyclohexanone oxime |
| $Cl$-cyclohexyl=$N-OH$ | 5-chloro-1-cyclohexanone oxime |
| cyclopentyl($C_2H_5$)=$N-OH$ | 2-ethyl-cyclopentanone oxime |

The more preferred oximes include, in particular, formaldehyde oxime, acetaldehyde oxime, acetone oxime, methyl ethyl ketone oxime, diethyl ketone oxime and cyclohexanone oxime.

Methyl ethyl ketone oxime is especially advantageous because the reaction product of this oxime, notably with methyltrichlorosilane or with vinyltrichlorosilane may be employed at ambient temperature as functionalization and crosslinking agent in many polymeric silicone compounds, especially for the production of cold-vulcanizable elastomers.

The process according to the present invention is generally carried out as follows, with reference to the attached Figure of Drawing which illustrates, by way of example and in a diagrammatic manner, an apparatus which can be employed for implementing the subject process.

The organic solvent selected is first supplied to the reactor 1, at the desired supply rate, after setting the stirrer 2 in motion and initiating the flow of the coolant liquid, generally water, in the condensers 3 and 4 and in the absorption column 5. The space within the reactor 1 is substantially at atmospheric pressure, this reactor being equipped with a device 6 for determining the temperature of the mass, and connection means which are known to prevent atmospheric moisture from penetrating therein. The solvent (from a reservoir which is not shown, the weight loss of which can be monitored) is introduced into the reactor 1 via the pipe 7 which is connected to a tubular 9 arranged on the upper part of the reactor 1. In the case shown, the solvent is thus introduced into the reactor 1 above the reaction mass; however, in another embodiment of the process, it is advantageous that the solvent is introduced into the lower section of the reactor 1. When the solvent has filled the reactor 1, i.e., when it has reached the overflow device 10, ammonia gas is introduced at the desired flow rate into the reactor 1 via inlet pipe 11 which opens into the lower part of the said reactor 1. The pipe 11 is provided with means 12 which make it possible to determine and adjust this flow rate of ammonia gas generally originating from a metal cylinder, the weight change of which is monitored. The overflow device 10 is advantageously supplied with an internal tubulure 13 extending to a small extent into the reaction mass so that vapors are not withdrawn through this overflow device 10. When the ammonia gas has saturated the solvent contained in the reactor 1, it exits the latter via the tubulure 14 connected to the condenser 3 which it traverses, passes through the pipe 15 bringing the upper part of the condenser 3 into communication with the lower part of the column 5 supplied with an internal packing, passes through the column 5 and the condenser 4 downstream thereof, and exits the apparatus via the pipe 16 which is equipped with means, which are not shown, for detecting and measuring the escape of the excess ammonia gas in the reaction and for preventing atmospheric moisture from entering into this pipe 16.

When ammonia gas escapes from the apparatus via the pipe 16, the oxime (of formula $R'R''C=N-OH$) charged to the pipe 17 by a proportioning pump 18 is then introduced, at the desired rate, into the upper part of the column 5 which oxime originates, for example, from a container, the weight changes of which can be monitored. The column 5 contains a packing, for example Rasching rings or the so-called Fenske helices, which are glass spirals cut at each turn, and marketed by PROLABO (catalog 1987, page 427).

The oxime is thus impregnated with ammonia gas before being introduced into the lower part of the reactor 1 via the inlet pipe 19. As soon as the oxime enters into the reactor, the proportioning pump 20 is actuated, which pump drives the halogenated silane (of formula $R_{4-n}SiX_n$) in the pipe 21 at the desired flow rate, this silane originating, for example, from a container, the weight changes of which are determined. The pipe 21 communicates into the lower part of the reactor 1.

The following are then further introduced into the reactor 1, simultaneously and at the desired rates: organic solvent, ammonia, oxime and halogenated silane.

The gravimetric ratio:

$$\frac{\text{solvent}}{R_{4-n}SiX_n}$$

generally ranges from 5 to 20, inclusive, whereas the ratio:

$$\frac{\text{number of moles of oxime}}{\text{number of moles of } R_{4-n}SiX_n \text{ multiplied by } n}$$

ranges from 1 to 1.2, preferably from 1.005 to 1.05, also inclusive.

Indeed, it is preferable to employ an excess of oxime to assure that silazanes are not formed.

For the safety of the process: the ratio:

$$\frac{\text{number of moles of } NH_3}{\text{number of moles of } R_{4-n}SiX_n \text{ multiplied by } n}$$

ranges from 1.04 to 1.46, preferably from 1.1 to 1.36, inclusive.

During the introduction of the above materials into the reactor 1, the reaction mass becomes hot and the vapors of the solvent can be refluxed by the condenser 3. The reactor 1 may optionally be provided with a jacket which enables it to be cooled; however, the process according to the present invention is advantageously carried out without having to cool the said reactor 1. A part of the reaction mass especially containing the ammonium halide of formula $NH_4X$ (formed during the reaction between the halogenated silane of formula $R_{4-n}SiX_n$, the oxime of formula $R'R''C=N-OH$ and ammonia) exits the reactor 1 continuously and inlets the container 22 via the pipe 23 which is connected to the overflow device 10 of the reactor 1. This container 22 contains an opening 24 which enables it to be placed at atmospheric pressure while preventing the entry of moisture into this container. This reaction mass, which is continuously withdrawn, is then filtered in order to remove the ammonium halide therefrom, which ammonium halide is rinsed with a solvent, advantageously the same solvent as that introduced into the reactor 1. The filtrate containing the solvent, the oxime (optionally, if an excess is employed) and the iminooxysilane formed, is then subjected to a distillation in order to separate therefrom the solvent which may be recycled into the reactor 1 via the pipe 7. If it is desired to isolate the iminooxysilane (the "oximinosilane"), the separation of the oxime and the oximinosilane is continued by more thorough distillation under vacuum. Insofar as a small amount of oxime in the iminooxysilane obtained does not interfere with the application envisaged (for example, as a crosslinking agent for silicone polymer), it is sufficient to determine the oximinosilane formed by chromatography, in the distillation residue after the organic solvent is removed. The yields of oximinosilane relative to the halogenated silane ($R_{4-n}SiX_n$) introduced into the reactor are generally greater than 80%. Moreover, the residence time of the reagents in the reactor 1 is less than one hour, preferably between 10 and 40 minutes.

In order to further illustrate the present invention and the advantages thereof, the following specific examples are given, it being understood that same are intended only as illustrative and in nowise limitative.

EXAMPLE 1

Preparation of

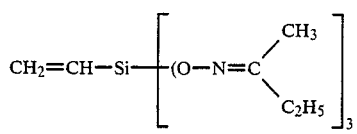

designated, in particular, vinyltris(methyl ethyl ketoximo)silane or vinyltris(2-butylideneiminooxy)silane.

The apparatus shown in the Figure of Drawing was used. The reactor 1 had a total volume of two liters and the overflow device 10 was positioned such that the volume of the reaction mass was one liter. The stirrer 2 had blades made of polytetrafluoroethylene and was rotated at 160 rpm.

The organic solvent selected viz., 1,1,2- trichloro-1,2,2-trifluoroethane, marketed by ATOCHEM under the trademark "Flugene 113" was first introduced into the reactor via the pipe 7, at a rate of 2,071.5 g/hr, after initiating the flow of the coolant water in the condenses 3 and 4 and the column 5, packed with Fenske helices, having a diameter of 4 mm over a height of 31 cm, the column having an internal diameter of 5 cm. When the flugene reached the overflow device 10, ammonia gas was passed into the reactor 1 at a flow rate of 91.5 g/hr (which amounted to 5.38 mole/hour) via the pipe 11 which communicated with the lower part of the reactor. When ammonia exited via the pipe 16, methyl ethyl ketoxime (of the formula

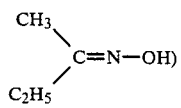

was introduced at a rate of 396.5 g/hr (which amounted to 4.56 moles per hour), at the upper part of the column 5 via the pipe 17. The ketoxime was introduced into the lower part of the reactor 1 via the pipe 19 after being impregnated with the ammonia gas which was supplied by the pipe 15 and which passed through the packing of this column 5 from the bottom upwards. Vinyltrichlorosilane (of the formula $CH_2=CH-SiCl_3$) was then introduced into the reactor 1 at a rate of 223 g/hr (which amounted to 1.38 mole/hour) through the pipe 21 which communicated with the lower part of the reactor 1.

All these materials were further introduced into the reactor 1 for a period of 2 hours, 30 min, at the rates mentioned above, the temperature of the reaction mass having been increased and stabilized at 49–50° C., while the flugene refluxed in the condenser 3.

In this experiment, the gravimetric ratio

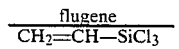

was 9.3, the ratio

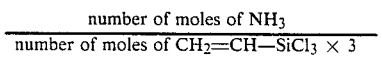

was 1.3 the ratio:

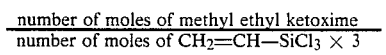

was 1.1.

The residence time of the products in the reactor was substantially 30 minutes.

During the introduction of the products into the reactor 1, the reaction mass, which was in the form of a slurry, continuously exited through the overflow device into the pipe 23, such as to be stored in the container 22. After 2 hr, 30 min, the entire reaction mass was filtered in order to remove therefrom the $NH_4Cl$ precipitate formed during the reaction. The cake obtained was washed with flugene and the liquid phase containing flugene, the excess ketoxime and the vinyltris(methyl ethyl ketoximo)silane formed was distilled.

The yield (by chromatography) of vinyltris(methyl ethyl ketoximo)silane relative to the vinyltrichlorosilane charged was 93%.

EXAMPLE 2

The procedure of Example 1 was repeated, except for the rate of supply of methyl ethyl ketoxime, which was 372 g/hr (which amounted to 4.28 moles per hour) and the rate of supply of vinyltrichlorosilane, which was 228 g/hr (which amounted to 1.41 moles per hour).

In this experiment, the gravimetric ratio

was 9.1, the ratio

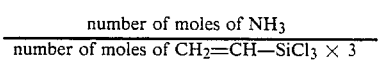

was 1.27, the ratio

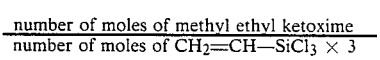

was 1.01.

The yield (by chromatography) of vinyltris(methyl ethyl ketoxime)silane relative to the vinyltrichlorosilane was 93%.

EXAMPLE 3

Preparation of

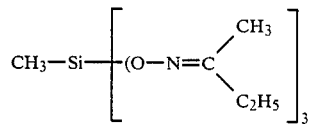

designated, in particular, methyltris(methyl ethyl ketoximo)silane.

The reaction was carried out in the same manner and with the same apparatus as that described in Example 1, replacing the vinyltrichlorosilane with methyl trichlorosilane.

The rate of supply were:

| (i) | flugene: | 2,071.5 g/hr; |
|---|---|---|

| (ii) | ammonia: | 91.5 g/hr (5.38 mole/hour); |
| (iii) | methyl ethyl ketoxime: | 372 g/hr (4.28 mole/hour); |
| (iv) | methyltrichlorosilane: | 211.5 g/hr (1.415 mole/hour); |

The residence time of the materials in the reactor was 30 minutes.

The gravimetric ratio $$\frac{\text{flugene}}{\text{methyltrichlorosilane}}$$

was 9.8. The ratio $$\frac{\text{number of moles of NH}_3}{\text{number of moles of methyltrichlorosilane} \times 3}$$

was 1.27. The ratio $$\frac{\text{number of moles of methyl ethyl ketoxime}}{\text{number of moles of methyltrichlorosilane} \times 3}$$

was 1.01.

The reagents were introduced continuously and simultaneously into the reactor for 3 hours.

The yield of methyltris(methyl ethyl ketoximo)silane relative to the methyltrichlorosilane charged was 93% (by chromatography).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the continuous production of oximinosilanes of formula $(R'R''C=N-O)_n-SiR_{4-n}$ comprising the steps of:
   (a) injecting continuously and simultaneously into a reactor equipped with a stirrer:
   an organic solvent,
   ammonia gas,
   a halogenated silane of formula $R_{4-n}SiX_n$ in which X represents a halogen and R represents an alkyl radical containing from 1 to 15 carbon atoms, an alkenyl radical containing from 2 to 15 carbon atoms, an aryl, aralkyl or cycloaklyl radical containing from 5 to 15 carbon atoms, it being possible for these radicals to optionally contain hydrogen atoms substituted by halogen atoms which are inert in the reaction of the process, n being equal to 1, 2, 3 or 4, and
   an oxime of formula $R'R''C=N-OH$, in which R' and R" may represent a hydrogen atom, an alkyl radical containing from 1 to 15 carbon atoms, an alkenyl radical containing from 2 to 15 carbon atoms, an aryl, cycloalkyl, cycloalkenyl, aralkyl or alkylaryl radical containing from 5 to 15 carbon atoms, these radicals being optionally substituted by halogen, atoms which are inert in the reaction, it being possible for R' and R" to together form an alkylene group such as $-(CH_2)_m-$, in which m represents 3 to 7, it being possible for the said methylene groups to contain hydrogen atoms substituted by halogen atoms which are inert in the reaction, the ratio $$\frac{\text{number of moles of NH}_3}{\text{number of moles of } R_{4-n}SiX_n \text{ multiplied by } n}$$

being between 1.04 and 1.46, the ratio $$\frac{\text{number of moles of oxime}}{\text{number of moles of } R_{4-n}SiX_n \text{ multiplied by } n}$$

being between 1 and 1.2;
   (b) continuously collecting the reaction mass which leaves the reactor with an overflow device; and
   (c) removing the precipitate of $XNH_4$ obtained from this reaction mass and distilling the organic liquid phase in order to recover therefrom the oximinosilane.

2. The process according to claim 1, in which the substances applied to the reactor are introduced into the lower part of the latter, and in which the ratio $$\frac{\text{number of moles of oxime}}{\text{number of moles of } R_{4-n}SiX_n \text{ multiplied by } n}$$

is between 1.005 and 1.05.

3. The process according to claim 1, wherein the gravimetric ratio:

$$\frac{\text{solvent}}{R_{4-n}SiX_n}$$

is between 5 and 20.

4. The process according to claim 1, in which the solvent employed has a boiling point below 60° C.

5. The process according to claim 1, in which the solvent employed is not flammable.

6. The process according to claim 1, in which the solvent employed is a perchloroflourinated aklane.

7. The process according to claim 6, in which the solvent employed is trichlorotrifluoroethane.

8. The process according to claim 1, in which the solvent recorded at (c) is redirected into the reactor.

9. The process according to claim 1, in which the excess ammonia gas escaping continuously from the reactor is brought into contact with the oxime before the latter is introduced into the reactor.

10. The process according to claim 1, in which the residence time of reagents in the reactor is less than 1 hour, preferably between 10 and 40 minutes.

11. The process according to claim 1, in which the halogenated silane employed is methyltrichlorosilane or vinyltrichlorosilane, while the oxime employed is methyl ethyl ketoxime.

12. The process of claim 1 wherein the halogenated silane contains an alkyl radical containing from 1 to 6 carbon atoms.

13. The process of claim 1 wherein the halogenated silane contains an alkenyl radical containing from 2 to 6 carbon atoms.

14. The process of claim 1 wherein the oxime contains an alkyl radical containing from 1 to 6 carbon atoms.

15. The process of claim 1 wherein the oxime contains an alkenyl radical containing from 2 to 6 carbon atoms.

* * * * *